(12) United States Patent
Casati

(10) Patent No.: US 6,341,529 B1
(45) Date of Patent: Jan. 29, 2002

(54) METHOD AND APPARATUS FOR MEASURING SUBSTRATE SURFACE CLEANLINESS

(75) Inventor: Donato Casati, Merate (IT)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/366,591

(22) Filed: Aug. 4, 1999

(30) Foreign Application Priority Data

Aug. 25, 1998 (GB) ............................................. 9818421

(51) Int. Cl.[7] ............................. G01N 3/00; G01N 3/08
(52) U.S. Cl. ................................................ 73/796; 73/826
(58) Field of Search ........................... 73/81, 796, 789, 73/862.393, 826, 831; 510/384, 385

(56) References Cited

U.S. PATENT DOCUMENTS 4,848,141 A * 7/1989 Oliver et al. ................... 73/81
5,959,215 A * 9/1999 Ono et al. ..................... 73/798

\* cited by examiner

Primary Examiner—Benjamin R. Fuller
Assistant Examiner—Maurice Stevens
(74) Attorney, Agent, or Firm—Schmeiser, Olsen & Watts; Lawrence R. Fraley

(57) ABSTRACT

A method and apparatus for estimating the degree of cleanliness of a substrate surface, particularly an inorganic surface used in the manufacturing of electronic components. A soft metal, eg., indium, probe is pressed against the substrate surface to be tested and then withdrawn. A tensile force, caused by the surface energies of the two materials, opposes the separation. If the inorganic surface is contaminated by any organic material, this force will be greatly affected. The tensile force is measured with a load cell and the displacement from the expected value will indicate the degree of contamination of the substrate surface.

19 Claims, 2 Drawing Sheets

METHOD AND APPARATUS FOR MEASURING SUBSTRATE SURFACE CLEANLINESS

TECHNICAL FIELD

The present invention relates to a method and apparatus for measuring the degree of cleanliness of a substrate surface.

BACKGROUND OF THE INVENTION

In the manufacturing process of microelectronic components, particularly in the assembly operation of integrated circuits, many operations require a cleaning step. However, even the most accurate cleaning method can leave some contamination. Many circumstances require that the cleanliness of a surface be tested and measured to verify that the contamination of the part is contained within acceptable limits. Furthermore, a check on the cleanliness of a surface may be required when a part is moved between processing steps where handling or transportation is required. For example, a cleaning or a check of the degree of cleanliness may be required before electroplating of a part, or before a component is soldered onto a plated pad. An example is the mounting of a chip (device) on a substrate, usually done through soldering. This is called "first level packaging". This stage of the process needs to be performed in a "clean" environment to avoid contamination of the parts, before the module is encapsulated, usually with a resin, and the circuits are protected by external agents.

The meaning of "clean" can vary significantly according to the application field considered. In precision cleaning applications, in which the required degree of cleanliness is very high, such as in the manufacture of medical components or electronic products, an accurate assessment of surface cleanliness is needed in order to meet the expected quality parameters.

In the manufacturing of electronic components and products, the contamination of a surface can be caused by a number of different factors. Examples of contamination include: the deposition of small particles; ionic contamination; deposition of chemical compound layers (e.g., oils or fluxes) occurring during the manufacturing steps; and adsorption of organic material (e.g., hydrocarbons or moisture) caused by exposure to the atmosphere. If a degree of cleanliness must be ensured, a reliable method of measurement of such degree is needed.

An accurate cleanliness assessment also helps in protecting the environment against pollution from cleaning agents, by evaluating new cleaning methods, or optimizing the existing cleaning processes.

Methods for measuring the degree of cleanliness can be divided in two categories: a) direct methods; and, b) indirect. Direct methods analyze the surface to be checked to discover whether the contamination of the surface exceeds a predetermined threshold. These methods are either dependent on human discretionary power, such as a magnified visual inspection, or require sophisticated and very expensive equipment. Indirect methods are based on the analysis of a very powerful solvent after it has been used to extract the contaminants from a specimen surface.

It should be immediately evident that the above described techniques are very labourious and, in the case of some direct methods, are not completely reliable, because of human intervention. Furthermore, the interruption of the mechanical handling of the modules for the manual checking and refinement, leaves open the eventuality of contamination during the waiting times and the moving of the modules. None of the methods mentioned above are useful to detect the contamination of organic adsorbed layers.

For the above reasons, a more accurate and reliable method would be highly desirable, particularly for the detection of organic contamination of the type described above. It is an object of the present invention to provide a technique which overcomes the above drawbacks.

OBJECTS AND SUMMARY OF THE INVENTION

An object of the present invention is to provide a method for measuring the degree of cleanliness on a substrate surface.

Another object of the present invention is to provide a method for measuring organic contamination on the surface of an inorganic substrate.

Another object of the present invention is to provide an apparatus to determine the degree of cleanliness of a substrate surface by applying a probe to a substrate with a compressive force and measuring the tensile force needed to separate the probe from the substrate surface.

A further object of the present invention is to provide a method of determining the degree of cleanliness of a substrate surface by providing a ratio between the tension force Fw and the pressure force Fi of contacting a substrate surface with a probe and comparing this ratio with a value for a clean surface.

According to one aspect of the present invention, there is provided a method for revealing and estimating contamination on a substrate surface comprising the steps of: bringing a probe in contact with a substrate surface; applying a compression force $F_i$ between the probe and the substrate surface; separating the probe and the substrate surface; measuring the tensile force $F_w$ which opposes the separation; and, comparing the tensile force measured with an expected value for a clean surface.

Further, according to another aspect of the invention, there is provided an apparatus for revealing contamination on a substrate surface and measuring the cleanliness of a substrate surface, comprising: a probe; a system for bringing said probe in contact with the substrate surface; a system for applying a compression force $F_i$ between the probe and the surface; a system for separating the probe and the substrate surface; and, a system for measuring the tensile force $F_w$ required to separate the probe and the substrate surface.

Further, according to yet another aspect of the invention, there is provided an apparatus for revealing contamination on a substrate surface and measuring the cleanliness of the substrate surface comprising: a first member; a substrate having a first surface and second bottom surface, the second bottom surface positioned on the first member; a second member; a probe positioned on said second member; a system for bringing together the substrate first surface and the probe and applying a compressive force; a system for applying a tensile force to separate the substrate first surface and the probe; a system for measuring the compressive force and the tensile force; and, control a system for controlling movement by the probe and the substrate.

BRIEF DESCRIPTION OF THE DRAWINGS

Various embodiments of the invention will now be described in detail by way of examples, with reference to accompanying figures, where.

DETAILED DESCRIPTION OF THE PREFERRED EMBODIMENT

For a better understanding of the present invention, together with other and further objects, advantages and capabilities thereof, reference is made to the following disclosure and appended claims in connection with the above-described drawings.

The present invention exploits the chemical-physical characteristics of the soft and stable metals, eg., indium. When two perfectly smooth, parallel and clean solid surfaces come in contact, these surfaces adhere to one another with an energy equal to the sum of their own surface energies. To separate the two surfaces, a force must be applied which counteracts the adhesion force. Inorganic surfaces have great surface energies, e.g., in the range of $10^3$ mJ/m$^2$, while organic surfaces have very low surface energies, e.g., in the range of $10^1$ mJ/m$^2$. As a consequence, if an organic material contamination is deposited on an inorganic surface, e.g., a metal, the adhesion force of the surface is highly reduced.

According to a preferred embodiment of the present invention, a test probe of soft metal, e.g., indium, is brought in contact with the surface to be analyzed and a pressure is applied to the probe. It is obvious that the surface could be equivalently pressed against the probe with the same effect.

The choice of a soft metal, e.g., indium, allows a good adhesion between the probe and the substrate surface. The pressure between the probe and the substrate surface, particularly if the surface is inorganic, generates a deformation of the indium probe head which shapes itself on the substrate surface, increasing the adhesion force. This adhesion force is measured by subsequently withdrawing the test probe from the surface and measuring the force opposing the separation. The adhesion force depends on the surface material and is proportional to the pressure applied in the contact between the indium surface and the substrate surface.

Figure 1:
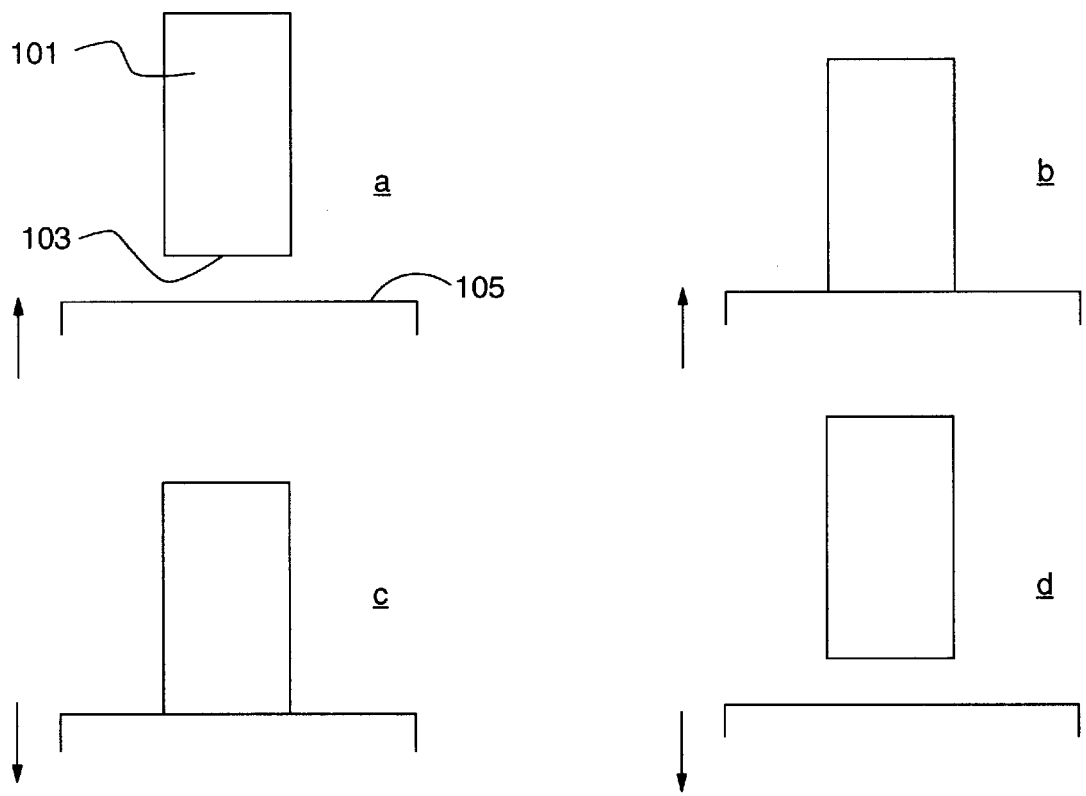
FIG. 1 shows schematically the various positioning relationships between the probe and a substrate surface according to a preferred embodiment of the present invention.

With reference to FIG. 1, in a preferred embodiment of the present invention, the test probe 101 has a flat head 103, made of pure indium with a radius of 0.5 to 2 mm. In the preferred embodiment of FIG. 1, a wire of indium, with a radius of 1.5 mm has been used. The probe is brought in contact with and pressed against the surface 105 to be tested at a constant speed $S_i$ of 0.1 to 1 mm/min until a predetermined force $F_i$ (e.g., 1 to 10 N) is reached. The pressure applied to the probe against the surface 105 deforms the indium head surface and helps in making the two surfaces better adhere. Then the probe 103 is withdrawn applying the same speed $S_i$ in the opposite direction. The tensile force $F_w$ needed to separate the probe 103 from the surface 105 is then measured. The weaker this tensile force $F_w$ will be, the greater the organic contamination. As mentioned above, the pressure applied (force $F_i$) greatly affects the adhesion force and consequently the force $F_w$ required. For this reason a more "independent" value could be desirable. According to a preferred embodiment, the ratio between the tension force $F_w$ and the pressure force $F_i$ (in absolute value) is used as an indication of the cleanliness degree of the surface. The ratio R is a unitless number, which in ideal conditions has a maximum value $R_0$. Any contamination of the surface 105 affects this value $R_0$, so the displacement value of R from $R_0$ is proportional to the "contamination" degree of the surface. The values of R can be normalized in order to have a scale between 0 and 1 or any other range of value desired.

Figure 2:
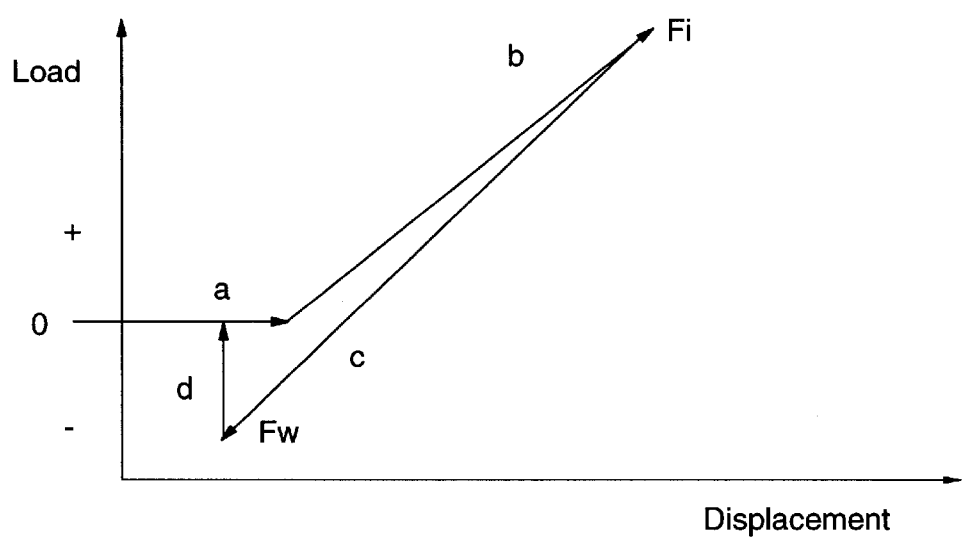
FIG. 2 shows the load-displacement curve representing the adhesion effect between two surfaces.

In FIG. 2, a load-displacement curve is shown. It is a representation of the adhesion effect when two surfaces are brought in contact and then withdrawn. The Y axis represents the force: the compression force for values higher than 0, and the tensile force for values less than 0. Displacement is represented on the X axis. In the first phase, corresponding to the segment "a" of the curve, the two surfaces are moving relatively towards each other: a force equal to 0 is measured. In the second phase, corresponding to the segment "b" of the curve, the surfaces are in contact and subject to a compression force; this force increases until a force $F_i$ is reached. In the third phase, corresponding to the segment "c" of the curve, the surfaces are moving relatively in the opposite direction and a force $F_w$ must be applied to completely separate the surfaces (phase "d").

As mentioned above, to maximize the adhesion effect between the indium probe and the substrate surface (e.g., having an inorganic surface), the indium probe head surface should be as flat as possible. One of the possible techniques is to smooth the head with an abrasive cloth, but contamination problems could arise. An alternative is to cut the probe, but the softness of the material makes it difficult to obtain a flat profile, e.g., if the indium probe is cut with a scalpel, a deformation often occurs. A solution to this deformation problem is to cool the indium wire to a very low temperature for stiffening the indium. In a preferred embodiment the indium wire is immersed in liquid nitrogen (−170° C.) and then immediately cut with a razor blade or a cryo-microtome.

Obviously, the soft metal probe should be completely clean to ensure that the ratio R is not affected by any impurity on the probe and reveals the contamination of the surface 105 instead of its own contamination. This is particularly important when the step of smoothing the indium head surface is performed in a non completely clean environment. Many precision cleaning technologies can be used for cleaning the indium probe. According to a preferred embodiment a plasma chemical cleaning is used. Plasma cleaning (or sputter cleaning) is caused by highly energetic ions which remove, by physical impact, all types of contamination atoms from a surface. As an alternative, the indium probe 103 could be cleaned by rinsing in organic solvent, then submitted to UV-Ozone cleaning in an UVOCS chamber(Ultra Violet Ozone Cleaning System), made by Uvocs Inc., Montgomeryville, Pa., allowing the probe head surface to be exposed to UV radiation for 4 to 8 minutes at a distance of 5 to 10 mm. The clean probe should then be used within a few minutes from this operation, being careful to avoid any possible re-contamination.

Figure 3:
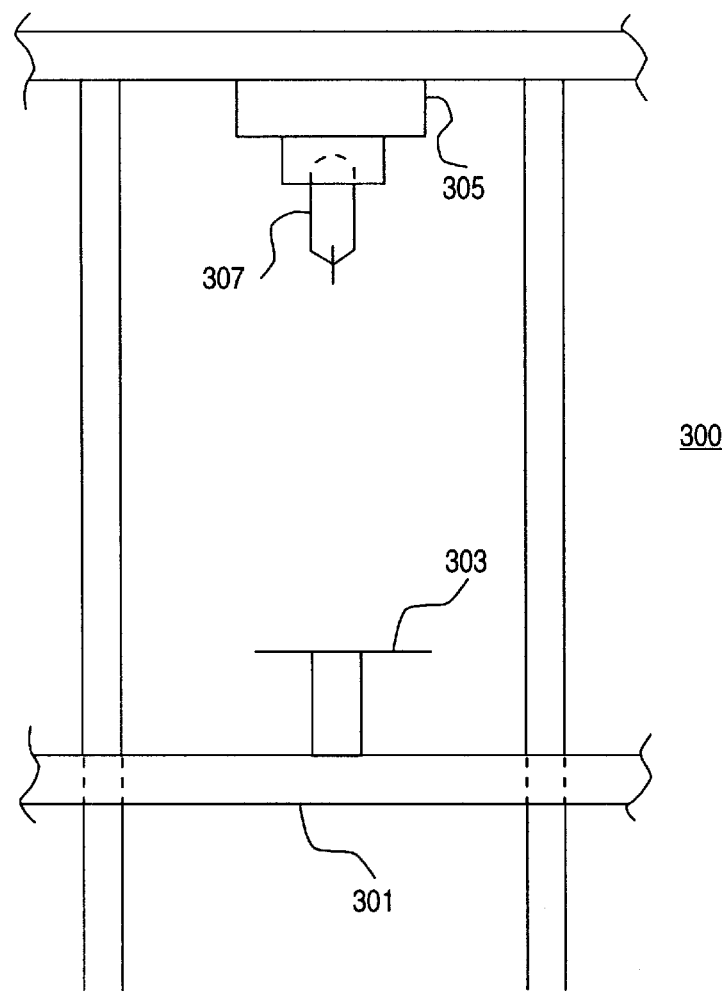
FIG. 3 shows schematically the measurement apparatus according to a preferred embodiment of the present invention; and, FIG. 4 shows the detail of the probe assembly of the measurement apparatus.
Figure 4:
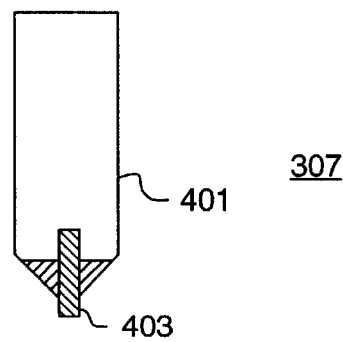

FIG. 3 represents a measurement apparatus 300 according to a preferred embodiment of the present invention. A crosshead member 301 carries the substrate surface 303 to be analyzed. The surface 303 could be, e.g., a gold plated conductive pad of a printed circuit board. A load cell 305 carries the soft metal probe assembly 307. A load cell is an apparatus which measures the tensile and the compression force applied. In the preferred embodiment of the present invention, the load cell 305 must reveal small forces in the range of mN. Many commercially available load cells may be used, e.g., an apparatus produced and commercialized by Instron Corp. of Canton, Mass.. The probe assembly 307 comprises a mandrel 401 and the soft metal probe, e.g., indium, probe 403 as detailed in FIG. 4. According to a preferred embodiment of the present invention, the probe 403 is an indium wire of 0.5 to 2 mm radius having a flat head previously smoothed and safely cleaned. According to the preferred embodiment of the present invention, the surface 303 is moved towards and pressed against the indium probe at a constant speed of 0.1 to 1 mm/s until a predetermined compression force, e.g., 1 to 10 N is revealed by the load cell 305. Then the surface is withdrawn from the indium probe at the same predetermined constant speed and the tensile force caused by the adhesion between the indium head surface and the surface 303 is measured by the load cell 305. A CPU, e.g., a personal computer, controls all the movements and the measurements of the apparatus 300. The tensile force measured by the load cell during the separation of the two surfaces gives accurate indications about the cleanliness of the surface 303. A tensile force much less than the expected one clearly indicates the presence of organic contamination on the inorganic surface (e.g. gold plated metallic pad). Those skilled in the art will appreciate that the parameters and the reference scale can be varied and adjusted to obtain better readable values. For example, according to the preferred embodiment of the present invention, the cleanliness of the surface is expressed as the ratio between the tensile force $F_w$ and the compression force $F_i$. The higher this ratio will be the cleaner the surface. This value could also be normalized, e.g. to obtain a value between 0 and 1 or between 1 and 10, or even compared to the expected value of ideally clean, smooth and parallel surfaces. Furthermore, any other method of measuring and any other apparatus able to reveal and measure the tensile and compression force between the two surfaces can be used instead of the above described one.

While there have been shown and described what are at present considered the preferred embodiments of the invention, it will be obvious to those skilled in the art that various modifications can be made therein without departing from the scope of the invention as defined by the appended claims.

What is claimed is:

1. A method for revealing and estimating contamination on a substrate surface comprising the steps of:
   bringing a probe in contact with a substrate surface;
   applying a compression force $F_i$ between said probe and said substrate surface;
   separating said probe and said substrate surface;
   measuring a tensile force $F_w$ which opposes said separation; and,
   comparing said tensile force measured with an expected value for a clean surface to provide an estimate of the contamination on the substrate surface.

2. The method of claim 1 further comprising the step of cleaning said probe before said contact with said substrate surface.

3. The method of claim 2 wherein said cleaning of said probe is done by high energy ions.

4. The method of claim 2 wherein said cleaning of said probe is done by rinsing said probe in solvent followed by UV-Ozone cleaning.

5. The method of claim 1 wherein the step of bringing said probe in said contact with said substrate surface is performed at a constant speed S.

6. The method of claim 1 wherein the step of said separating said probe from said substrate surface is done at the constant speed S.

7. The method of claim 1 further comprising the step of expressing a degree of cleanliness of said substrate surface as a ratio between said tensile force $F_w$ and said compressive force $F_i$.

8. An apparatus for revealing contamination on a substrate surface and measuring a cleanliness of said substrate surface, comprising:
   a probe;
   means for bringing said probe in contact with said substrate surface;
   means for applying a compression force $F_i$ between said probe and said substrate surface;
   means for separating said probe and said substrate surface;
   means for measuring a tensile force $F_w$ required to separate said probe and said substrate surface; and
   means for comparing the measured tensile force $F_w$ to an expected value to provide a measure of the cleanliness of said substrate surface.

9. The apparatus of claim 8 wherein said probe is a soft metal.

10. The apparatus of claim 9 wherein said soft metal is indium.

11. The apparatus of claim 10 wherein the soft metal probe has a flat head.

12. The apparatus of claim 8 wherein said substrate is comprised of inorganic material.

13. The apparatus of claim 12 wherein said contamination being revealed is organic.

14. An apparatus for revealing contamination on a substrate surface and measuring a cleanliness of said substrate surface comprising:
   a first member;
   a substrate having a first surface and second bottom surface, said second bottom surface positioned on said first member;
   a second member;
   a probe positioned on said second member;
   means for bringing together said substrate first surface and said probe and applying a compressive force;
   means for applying a tensile force to separate said substrate first surface and said probe;
   means for measuring said compressive force and said tensile force;
   control means for controlling movement by said probe and said substrate; and
   means for comparing the measured tensile force to an expected value to provide a measure of the cleanliness of said substrate surface.

15. The apparatus of claim 14 wherein said probe is comprised of a soft metal.

16. The apparatus of claim 15 wherein said soft metal is indium.

17. The apparatus of claim 16 wherein said substrate first surface is comprised of an inorganic material.

18. The apparatus of claim 14 wherein said means for measuring said compressive force and said tensile force is a load cell.

19. The apparatus of claim 14 wherein said control means is a CPU.

* * * * *